(12) United States Patent
Berke

(10) Patent No.: US 7,240,554 B2
(45) Date of Patent: Jul. 10, 2007

(54) METHOD AND DEVICE FOR SIZING A CRACK IN A WORKPIECE USING THE ULTRASONIC PULSE-ECHO TECHNIQUE

(75) Inventor: Michael Berke, Bruhl (DE)

(73) Assignee: GE Inspection Technologies Systems GmbH (DE)

( * ) Notice: Subject to any disclaimer, the term of this patent is extended or adjusted under 35 U.S.C. 154(b) by 148 days.

(21) Appl. No.: 10/539,537

(22) PCT Filed: Sep. 29, 2003

(86) PCT No.: PCT/DE03/03238

§ 371 (c)(1),
(2), (4) Date: Jun. 17, 2005

(87) PCT Pub. No.: WO2004/055508

PCT Pub. Date: Jul. 1, 2004

(65) Prior Publication Data

US 2006/0230831 A1    Oct. 19, 2006

(30) Foreign Application Priority Data

Dec. 17, 2002  (DE) ............................... 102 59 218

(51) Int. Cl.
*G01N 29/00*  (2006.01)
(52) U.S. Cl. .............................. 73/602; 73/599; 73/600
(58) Field of Classification Search .................. 73/602, 73/598, 599, 600, 615, 616, 618, 606
See application file for complete search history.

(56) References Cited

U.S. PATENT DOCUMENTS 4,803,638 A * 2/1989 Nottingham et al. ......... 702/36

(Continued)

FOREIGN PATENT DOCUMENTS

DE    23 42 796    3/1975
GB    1 402 495    8/1975

OTHER PUBLICATIONS

API Recomended Practice 5UE, First Edition, American Petroleum Institute, Mar. 2002, p. 1-16.

(Continued)

*Primary Examiner*—Hezron Williams
*Assistant Examiner*—Jacques M. Saint-Surin
(74) *Attorney, Agent, or Firm*—Akerman Senterfitt

(57) ABSTRACT

The invention relates to a method for determining the size of a fracture (26) in a workpiece (20), in particular the depth of a fracture (26) in said workpiece (20), by means of the ultrasound pulse method, comprising the following method steps: a workpiece (20), with a front surface (22) and a back surface (24), having a fracture (26), extending from the back surface (24) and an angle test head (28) is applied to the front face (22), transmits ultrasound pulses at an angle alpha into the workpiece (20) and receives echoes from said pulse, the angle test head (28) is moved at least once over the fracture (26), such that the radiation beam (46) from the angle test head (28) completely covers the fracture (26), the received echo signals are digitized and stored in a memory (40) as variable pairs of echo signal versus runtime, the variable pairs form a value upwardly defined by an envelope (48) and the dimension of the fracture (26) is determined from the width of the envelope (48) at a given partial amplitude and the maximum amplitude of the envelope (48).

8 Claims, 2 Drawing Sheets

U.S. PATENT DOCUMENTS

Figure 1:
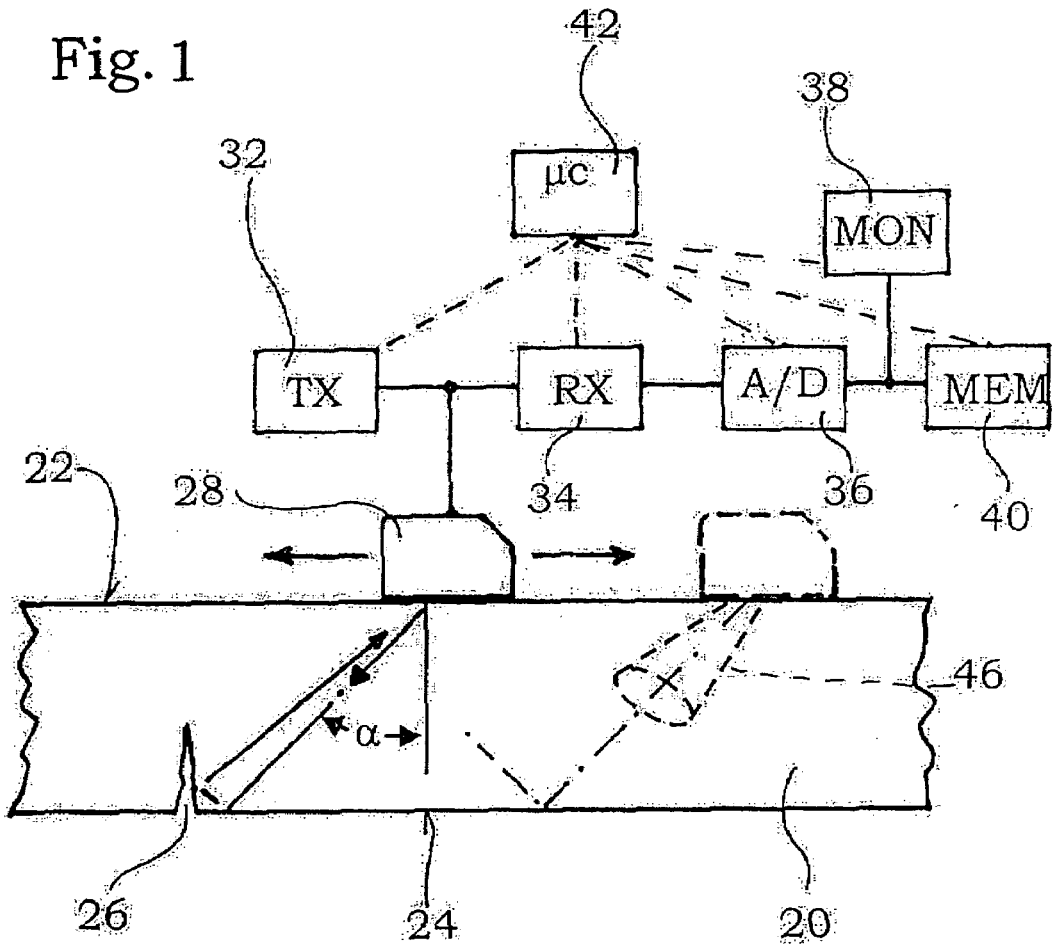

| | | | | |
|---|---|---|---|---|
| 4,947,351 A | * | 8/1990 | Moran et al. | 702/39 |
| 5,383,366 A | * | 1/1995 | Wallingford et al. | 73/602 |
| 5,629,865 A | * | 5/1997 | Roth | 702/56 |
| 6,382,028 B1 | * | 5/2002 | Wooh et al. | 73/602 |
| 6,877,377 B2 | * | 4/2005 | Dittrich et al. | 73/602 |

OTHER PUBLICATIONS

V. Deutsch, et al., Ultraschallprufung (1997) pp. 55-73.

V. Deutsch, et al., Ultraschallprufung (1997) pp. 125-135.

\* cited by examiner

METHOD AND DEVICE FOR SIZING A CRACK IN A WORKPIECE USING THE ULTRASONIC PULSE-ECHO TECHNIQUE

The invention relates to a method for sizing a crack in a workpiece using the ultrasonic pulse-echo method and to a device for carrying out this method.

The ultrasonic pulse-echo method is well known, the reader is referred to the DE-Book Krautkrämer and Krautkrämer "Werkstoffprüfung mit Ultraschall" ("Material Inspection with Ultrasounds"). A probe emits ultrasonic pulses. These pulses are at least partially reflected from a discontinuity, such as from an inner break, a crack or any other material flaw, and are again received by the same probe. They are evaluated with regard to the echo amplitude, at need taking their travel time into consideration.

It is also known to size a discontinuity using the so-called half-amplitude technique. The central beam of the probe is assumed to meet an edge of the discontinuity at the very moment when the amplitude of the echo has dropped from the maximum value it had upon fully detecting the discontinuity to half said value, meaning to −6 dB. This half-amplitude technique however requires the movement of the probe relative to the workpiece to be registered. Additionally, the travel time of the echo signals received may be taken into consideration for sizing a discontinuity.

A method of sizing cracks is known from the specifications of the American Petroleum Institute "Recommended Practice for Ultrasonic Evaluation of Pipe Imperfections", by which an angle beam probe is displaced across the crack so that its radiation beam moves across the crack. In a first way of performing this proposed measurement, in what is termed an A-scan, the maximum echo amplitude is looked for and recorded and the associated travel time noted down on the one side and the travel times of the echo signals that correspond to exactly half the maximum amplitude are noted down on the other side. The method is quite complicated. In a second embodiment, an envelope curve is drawn, the prerequisite being an ultrasonic apparatus that has a device for storing the maximum amplitudes such as a storage oscillograph. The thus obtained envelope curve is evaluated using a gate or an evaluation screen. The evaluation screen is set to 50% of the maximum amplitude of the envelope curve that commences at the intersection with the rising flank of the envelope curve and ends at the intersection with the falling flank of said envelope curve. To calculate the size of the flaw, the value of the sound velocity is varied until the evaluation screen sufficiently coincides with the envelope curve. Generally, this method is described to be lengthy and is only recommended for cracks the dimension, more specifically the depth, of which cannot be determined otherwise. The size of the flaw is calculated from a formula that takes into consideration the product of the maximum amplitude and of the time interval between the two 50%-amplitudes.

Although the hereto before known methods provide dimensions for cracks, they present disadvantages in practice. This is where the invention comes in. It is its object to indicate a method for detecting the size of cracks, more specifically for detecting the depth of a crack, that directly yields a value without major computation, that is, that quickly determines an initial value and is suited for an automatic method.

The solution to this object is achieved by

In accordance with the invention, the echo signals are digitalized and are stored in a memory as pairs of values over the travel time. If the angle beam probe sweeps across the entire crack once, one obtains a plurality of pairs of values that are limited toward the top by an envelope curve.

In a preferred manner of performing the invention, only the maximum amplitude values for the discrete travel times are stored, that is, but the envelope curve is stored.

The size of the flaw may now be determined directly from the envelope curve; this can be achieved by means of a computer module provided in the ultrasonic apparatus. The size of the flaw is proportional to the product of maximum amplitude and the half-width of the envelope. The proportionality factor is determined by measuring cracks the depth of which is known. This permits to find out the size of a crack in a workpiece without major manual adjustments and irrespective of the skill of the respective ultrasonic operator. The method is suited for extensive, preferably for full, automation.

As contrasted with the prior art method, it is no longer necessary to adjust the maximum reference amplitudes to 80% of the monitor height. The maximum echo amplitudes can be measured and stored at high resolution. A half-line can be calculated directly and be displayed on a monitor. The half-width of the envelope can be directly determined automatically and also be displayed on the monitor.

It is possible to change the amplification factor of the ultrasonic apparatus without the computation performed in the apparatus yielding erroneous results with regard to the crack depth. If, as this may happen in practice, the maximum echo amplitude of the flaw echo is either too high, that is, if it is in excess of 100%, or if it is too small (if the dynamic curve of the echo is too flat), the amplification of the ultrasonic apparatus is varied. The change in the amplification dV is registered. As the amplification changes dV, the maximum amplitude of the flaw echo must be converted according to formula 1

$$A_{max} = A'_{max} \times 10^{-dV/20}$$

wherein $A_{max}$ is the amplitude before changing the amplification and $A'_{max}$ the amplitude after the amplitude has been changed.

It has been found out that angle beam probes having a flat emission angle are advantageous. They need to be displaced over a larger distance than angle beam probes having smaller emission angles.

It has been found advantageous to check the envelope obtained and stored as such in the memory by means of an evaluation device such as an evaluation screen in order to see whether the angle beam probe has been moved sufficiently away from the crack so as to obtain on either side of the envelope a value that corresponds to the echo signal without the detected crack exerting any influence. The corresponding electronic evaluation circuit detects on the one side that the envelope falls to zero and on the other side that this actually occurs on either flank of the envelope. These checks can be performed automatically by the very inspection instrument without the operator influencing them. The inspection instrument stores the zero line obtained when no crack could be found. If a crack has been found, it checks whether the envelope drops to zero on either side. If this is not the case, a corresponding signal is delivered to the operator who reacts by moving the angle beam probe further away from the crack that has been detected until it reaches a region in which the detected crack is no longer noticeable on the level of the echo signal.

In an altered embodiment of the invention, an array consisting of a quite large number of individual probes is utilized instead of one angle beam probe. Said individual probes are triggered in such a manner that either the same effect is obtained as by displacing an angle beam probe across the surface, that is, by having the main beam parallely offset, or that the angle of the beam is varied. In both cases, mechanical movement relative to the surface is no longer necessary. Put another way, arranging a plurality of individual probes behind each other in an array replaces the need for displacement using one single probe.

Figure 2:
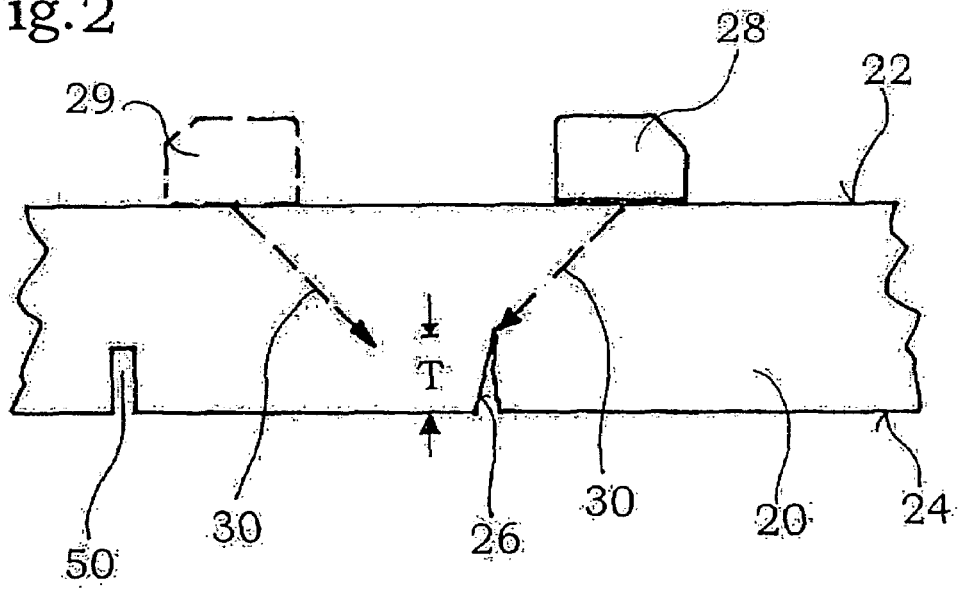
Figure 3:
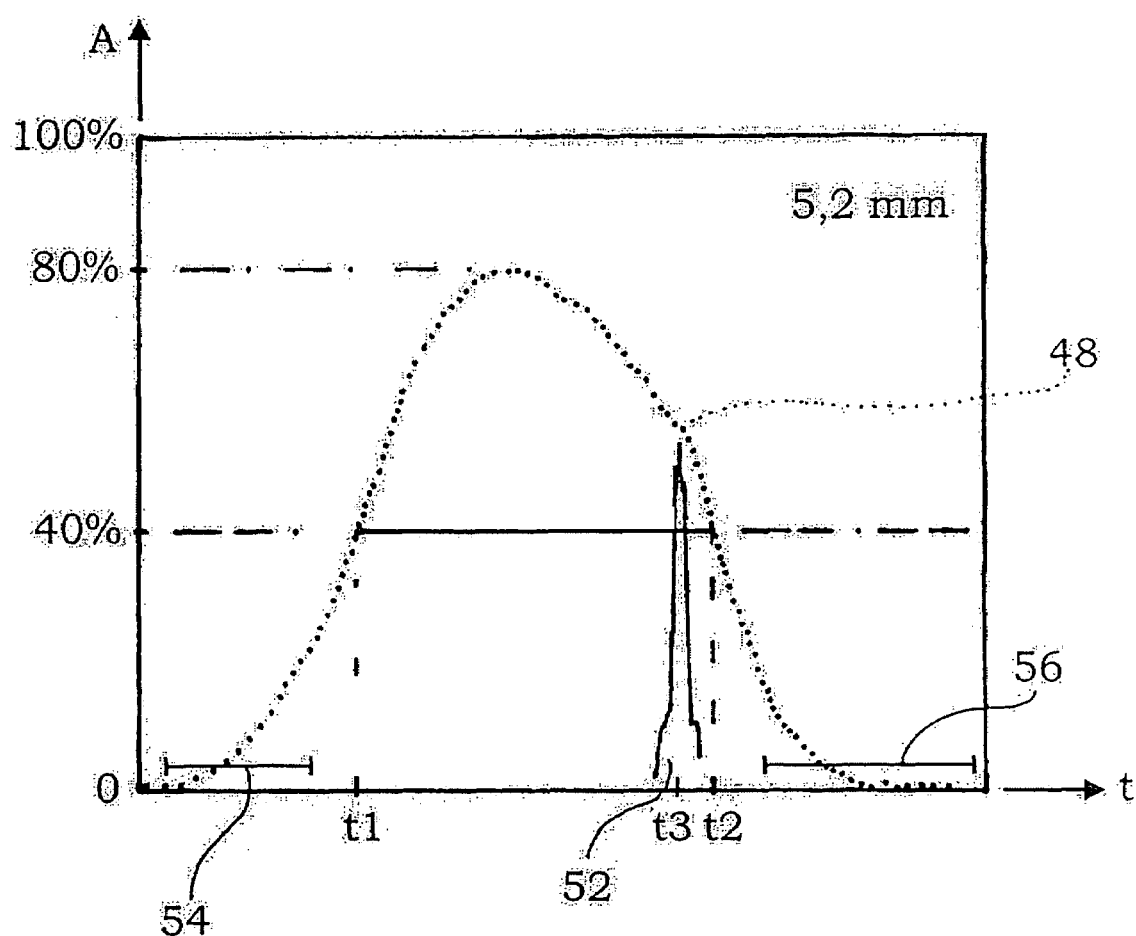

The invention will be understood better upon reading the following description with reference to exemplary embodiments. These exemplary embodiments are not intended to limit the scope of the invention in any manner. In the drawing:

FIG. 1 illustrates an array for ultrasonic inspection having a probe that is placed onto a workpiece having a crack; it also shows the path of the main beam of said probe, FIG. 2 is an illustration like FIG. 1, but in another position of the probe relative to the crack, FIG. 3 is an illustration of an envelope curve where the maximum echo amplitude A achieved (in Volt or %) is plotted down the side of the diagram whereas the respective travel time t (in ms) is plotted on the horizontal axis, with detection of the half-width and of the maximum amplitude being plotted.

A workpiece 20 can be seen in the FIGS. 1 and 2, said workpiece having a front face 22 and a back face 24. Typical examples of such type workpieces are tubes, such as tubes with quite large diameters, e.g., with diameters ranging from 20 to 80 cm. Typically, these tubes are oilfield pipes, tubes for pipelines, but also sheet metal and items for any application.

The crack 26 in the workpiece 22 commences on the back face 24 thereof. It also may be an internal crack that has no connection with the back face 24.

An angle beam probe 28 is placed on the front face 22. Along a main beam 30 located in the centre of a radiation beam of the probe 28, it sends ultrasonic pulses into the volume of the workpiece 20 at an angle alpha. The probe 28 is what is termed a transmit-receive probe, also referred to as a T/R-probe, so that it serves both for emitting and for receiving ultrasonic pulses.

The angle beam probe 28 is connected on the one side to a transmitter module 32, also referred to as TX, and on the other side to a receiver module 34, also referred to as RX. An analogue-to-digital converter 36, also referred to as A-D converter, is connected at the output of the receiver module. A monitor 38 for displaying an A-scan and an envelope, which is also referred to as MON, is connected to the output of said converter on the one side. On the other side, there is also connected to this output a memory 40, also referred to as MEM. Via well known suitable circuitry, data stored in the memory 40 can be displayed on the monitor 38, said monitor 38 however also displaying the A-scan respectively obtained from the inspection being performed. Finally, there is provided a computer module 42 that is also referred to as microcomputer or µC. It is connected to all of the electronic modules of the ultrasonic inspection apparatus; this is shown in dashed lines. The parts 32-42 thereby form the ultrasonic inspection apparatus. Its structure is actually known so that this apparatus will not be discussed in further detail. A typical example of an ultrasonic inspection apparatus that may be utilized for performing the method is the instrument USM 25 of the applicant.

FIG. 1 also shows a second position of the probe 28 that is labelled at 29. During inspection, the probe 28 is moved along the arrows 44. The movement must be large enough to pass over the crack 26. At the angle beam probe, which is shown in a dashed line, a radiation beam 46 is outlined in addition to the main beam 30. The reader is referred to the DE-Book mentioned herein above for a definition of a radiation beam. From the position shown in a dashed line, the probe is displaced during inspection sufficiently far to pass over the crack 26 and again reach a position in which it is located outside of the crack 26, meaning in which it is located at the same distance as the dashed position of the angle beam probe 28, but on the other side. It should be noted here that the dashed position is very far away and that it is possible that the crack 26 be again detected in the dashed position, but now after the main beam 30, which is shown in a dash-dot line, has been reflected at first from the back face 24, then from the front face 22 and from there toward the crack 26.

In practice, during inspection, the emission angles alpha are about 45° and typically range from 45-60°. This however does not mean that other angles alpha are excluded. The probe frequencies are in the MHz range, for example 1-5 MHz. The ultrasonic pulses are emitted at a repetition frequency of 50-100 Hz, with much higher frequencies being possible; the same applies for lower frequencies.

An inspection method is run as follows:

As can be seen from FIG. 1, the probe 28 emits ultrasonic pulses along the main beam 30. These ultrasonic pulses impinge either directly the crack 26 or the back face 24. In both cases, they are reflected toward the back face 24 or toward the crack 26 and are caused to return into the probe 28 after angular reflection. In the position as shown in FIG. 1, the main beam 30 first travels toward the back face 24, from there, after reflection, it travels along a short path to the crack 26 and from there back into the probe.

Each position of the probe 28 leads to an echo signal at a certain travel time. Each new position has another travel time and another value for the echo signals. The echo signals received by the receiver module 34 are amplified there and then digitalized in the A-D converter 36. In the memory 40, only the maximum amplitudes for one position of the probe and, as a result thereof, for one travel time are stored. Concurrently, the monitor displays the A-scan of the pulse that has just been emitted and/or the maximum values of all of the measurements performed during movement along the arrows 44. The maximum amplitudes for all the occurring travel times form an envelope curve 48 such as illustrated in FIG. 3.

FIG. 2 shows the relative position between probe 28 and crack 26 in which the main beam 30 strikes the tip of the crack 26, whereas in FIG. 1 the probe 28 is in a position in which it is quite near the root of the crack 26. In the position as shown in FIG. 2, about half of the radiation beam 46 is led past the crack 26 provided that the crack has a corresponding geometry, with about half the radiation beam being reflected into the probe 28. This leads to an amplitude of the echo signal that is about 50% less than the maximum amplitude. The maximum amplitude is for example typically achieved in the position of the probe 28 as shown in FIG. 1. It can be seen that the position in FIG. 2 is a position permitting to detect the half-width t2-t1 of the flaw.

FIG. 2 also illustrates in a dashed line a probe 29 offset by 180° together with its main beam 30. This is to make it obvious that the crack 26 can also be detected from the other side. The two measurements as outlined in FIG. 2 can be combined; the mean value of the flaw depth obtained for the two directions of emission can be outputted as the flaw depth T.

FIG. 2 also illustrates an intentionally introduced test flaw 50; it is a serration of known depth and width. It serves to set the ultrasonic instrument. This setting is performed as follows:

The flaw depth T50 of the test flaw is known. The test flaw 50 is now inspected using the inspection method; an envelope curve is established, which is similar to the envelope curve for the flaw 26 of FIG. 3. In the envelope curve 48 shown therein, a half-width is plotted at 50% of the maximum amplitude. It commences at the overall travel time t1 and ends at the overall travel time t2. This is performed in the same manner for the envelope curve of the test flaw 50. Now, a proportionality factor k is computed from the quotient of the depth of the test flaw divided by the half-width of said test flaw. This permits to now determine the flaw depth T of the crack 26 using the rule of three or the proportionality factor k according to the formula $T = k \times \text{half-width of the crack.}$ Put another way, the half-width obtained from the envelope curve shown in FIG. 3 is multiplied by the proportionality factor k; the result is the crack depth T. The crack depth T is directly displayed on the monitor 38; in FIG. 3, the value 5.2 mm is indicated by way of example.

In FIG. 3, the maximum amplitude of the envelope curve 48 is 80%; accordingly, the half-amplitude is 40%. At other maximum amplitudes, the computer module 42 computes the associated half-amplitude. Moreover, the amplification can be varied according to the formula indicated herein above.

FIG. 3 further illustrates an actual echo 52 as it usually appears on the A-scan. It does not entirely attain the height of an amplitude value measured at an earlier stage for the same travel time t3, so that it would not be taken into consideration for being stored in the memory 40.

The half-width t2 minus t1 is automatically calculated in the computer module 42. For this purpose, current computations, which are known in the art, are to be performed; they need not be discussed herein.

The envelope curve is also referred to as echo dynamic curve. The product of the half-width and of the maximum amplitude is multiplied by the proportionality factor k; the result is the crack depth.

The method has the advantage that an inspection report on the ultrasonic inspection performed may additionally include the stored envelope curves and so on. Improved documentation is thus made possible. It is also possible to evaluate the envelope curves at a later stage from other viewpoints.

Finally, FIG. 3 also shows two evaluation thresholds 54 and 56 at the base of the envelope curve 48. They are located so as to lie just above the zero line. They are intersected by the envelope curve so that the envelope curve is both above and beneath the thresholds. This is to make certain that the envelope curve is completely registered, that is, that the probe has been moved sufficiently away from the crack 26. This is advantageous for automatically performed measurements. It is however to be understood that it suffices in principle to register the envelope curve 58 until just beneath the half-value, this being sufficient for the measurement in accordance with the invention.

The invention claimed is:

1. A method for determining the size of a crack in a workpiece, using the ultrasonic pulse-echo method, said method involving the following method steps:

a workpiece is chosen having a front face and a back face, wherein the workpiece exhibits a crack starting at the back face, an angle beam probe is placed on the front face, the angle beam probe sends ultrasonic pulses at an angle alpha into the workpiece and receives echo signals of said pulses, the angle beam probe is moved at least once over the crack so that the radiation beam of the angle beam probe sweeps across the entire crack, the received echo signals are digitalized and stored in a memory as pairs of echo signal values over travel time, whereby the stored pairs of values form a multitude and an envelope curve is constructed of this multitude, wherein for the construction of the envelope curve the high values of the stored pairs are used, and the size of the crack is calculated from the width of the envelope curve at a predetermined partial amplitude and from the maximum amplitude of the envelope curve, wherein the size of the crack is proportional to the product of the maximum amplitude of the envelope curve and the width of the envelope curve at 50% of the maximum amplitude.

2. The method as set forth in claim 1, wherein several echo amplitudes are obtained for an individual value of the travel time, and wherein only the echo amplitude having the highest value is stored.

3. The method as set forth in claim 1, wherein the angle beam probe is a component part of an ultrasonic inspection apparatus, wherein said ultrasonic inspection apparatus further comprises a computer module and wherein said computer module outputs an output value representing a flaw size.

4. The method as set forth in claim 1, wherein the angle beam probe is moved several times across the crack.

5. A device for carrying out the method as set forth in claim 1 for determining crack in a workpiece using the ultrasonic pulse-echo technique, said device comprising:

an angle beam probe being a component part of an ultrasonic inspection apparatus which ultrasonic inspection apparatus is further comprised of the following parts:

a) a transmitter module and a receiver module, b) an A/D (analog-digital) converter that is connected downstream of the receiver module, c) a memory for storing values echo signals which values echo signals are in the form of pairs and are received from the transmitter module and are digitalized by the A/D converter together with the respective travel time, only the highest echo amplitude obtained being stored for every individual travel time and d) a computer module for computing the depth of the crack out of the maximum amplitude stored and from a width dimension of the envelope curve as stored.

6. The device as set forth in claim 5, wherein the ultrasonic apparatus comprises a monitor for displaying the envelope curve.

7. The method as set forth in claim 1, wherein the angle beam probe is moved several times back and forth over the crack.

8. The method as set forth in claim 1, wherein the depth of a crack in said workpiece is determined.

* * * * *